United States Patent [19]

Puritch et al.

[11] Patent Number: 4,576,950
[45] Date of Patent: Mar. 18, 1986

[54] ALKYL PYRIDINIUM SYNERGISTS FOR BENZIMIDAZOLE PESTICIDES

[75] Inventors: George S. Puritch, Brentwood Bay; Edward S. Kondo, Orleans, both of Canada

[73] Assignee: Safer Agro-Chem Ltd., Victoria, Canada

[21] Appl. No.: 561,083

[22] Filed: Dec. 14, 1983

[51] Int. Cl.⁴ ............................................. A01N 43/40
[52] U.S. Cl. .................................................... 514/358
[58] Field of Search ........................ 424/263; 514/358

[56] References Cited

U.S. PATENT DOCUMENTS

| | | | |
|---|---|---|---|
| 3,687,966 | 8/1972 | Haubein | 424/200 |
| 3,930,010 | 12/1975 | Klopping | 514/388 |
| 4,028,464 | 6/1977 | Bell et al. | 514/388 |
| 4,044,145 | 8/1977 | Lacroix | 514/391 |
| 4,060,624 | 11/1977 | Klopping | 514/388 |
| 4,060,625 | 11/1977 | Klopping | 514/388 |
| 4,078,070 | 3/1978 | Albrecht et al. | 514/388 |
| 4,105,775 | 8/1978 | Albrecht et al. | 514/388 |
| 4,107,318 | 8/1978 | Albrecht et al. | 514/388 |
| 4,164,582 | 8/1979 | Harju-Jeanty | 514/388 |
| 4,241,083 | 12/1980 | Morikawa et al. | 424/309 |

*Primary Examiner*—Leonard Schenkman
*Assistant Examiner*—Joseph A. Lipovsky
*Attorney, Agent, or Firm*—Larson and Taylor

[57] ABSTRACT

There is disclosed a fungicidal composition comprising (A) a fungicidal benzimidazole compound of the formula

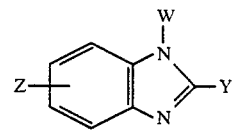

wherein W is H, or alkyl carbamoyl; Y is H, halogen, alkyl, alkoxy, alkyl thio, thiol, carbamic acid ester or hydroxy; Z is H, halogen or alkyl; and (B) a synergist alkyl pyridinium salt of the formula

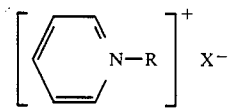

wherein R is an alkyl containing 8 to 20 carbon atoms; and X is a monovalent anion.

9 Claims, No Drawings

ALKYL PYRIDINIUM SYNERGISTS FOR BENZIMIDAZOLE PESTICIDES

FIELD OF THE INVENTION

This invention relates to a fungicidal composition based on the synergistic combination of alkyl pyridinium compounds with benzimidazole compounds. This combination provides increased effectiveness and activity against benzimidazole-tolerant fungi.

BACKGROUND OF THE INVENTION

The benzimidazole fungicides are used throughout the world under several brand names, including Benoyml and lignasan. These compounds can control a variety of fungal pathogens on vegetables, fruits and trees, including grey mould (*Botrytis cinerea* Pers.), powdery mildews (Erisyphe, Sphaerotheca), Dutch Elm Disease (*Ceratocystis ulmi*), brown rot (*Monilinia fructicola*) etc. Unfortunately, the fungidical effectiveness of the benzimidazoles has been significantly reduced due to the development of resistant fungal strains. The cause of this resistance has been attributed to a lack of penetration of the benzimidazoles through the outer fungal membranes (See Gessler, Phytopath. Z., 85: 35–38 (1976)).

A combination of benzimidazole fungicides and surfactants is known in the art, for example, U.S. Pat. No. 3,930,010 to H. L. Klopping teaches that the fungicidal activity of the benzimidazole compound is improved by combination with a surfactant at or above its critical micelle concentration (CMC).

Accordingly an object of the present invention is to provide a fungicidal composition containing as the main ingredient a fungicidal benzimidazole compound, the activity of which is increased by the addition of a synergist.

Another object of the present invention is to provide a method of combatting fungi employing a fungicidal benzimidazole compound, the effectiveness of which is enhanced by the addition of a synergist against fungi including benzimidazole-susceptible as well as benzimidazole-tolerant or -resistant fungi.

Still another object of the present invention is to provide a method for restoring or recovering the fungidical activity of the benzimidazole fungicide against benzimidazole-tolerant or -resistant fungi.

These and other objects of the present invention will be apparent to the person skilled in the art from the subsequent detailed description of the invention.

It has now been found that the mixture of benzimidazoles with alkyl pyridinium salts provides a unique combination that eliminates the fungal resistance factor and substantially improved the effectiveness of the fungicidal activity of the benzimidazole compounds, even at a concentration of the alkyl pyridinium salts far below its critical micelle concentration (CMC) level.

SUMMARY OF THE INVENTION

The present invention provides a composition comprising:

A. a fungicidal amount of a benzimidazole compound with the following general formula:

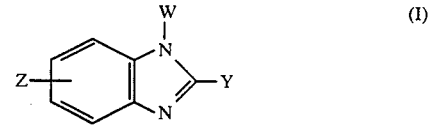

wherein W represents a hydrogen or lower alkyl carbamoyl, Y represents a hydrogen, or halogen atom, or lower alkyl, or lower alkoxy or lower alkyl thio or thiol radical or a lower alkyl carbamic acid ester or hydroxy group and Z represents a hydrogen, halogen atom or lower alkyl radical, or an acid addition salt or an alkali or alkaline earth metal salt of the compound of formula (I), and B. an alkyl pyridinium salt of the general formula:

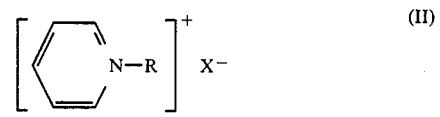

wherein R represents an alkyl radical containing 8 to 20 carbon atoms and X represents a monovalent anion, in an amount sufficient to enhance the effectiveness of the fungicidal activity of the above benzimidzole compound, and a carrier.

An embodiment of the invention provides a method of combatting fungi, which comprises applying a fungicidally effective amount of a benzimidazole compound of formula (I) and an alkyl pyridinium salt in an amount sufficient to enhance the effectiveness of the fungicidal activity of the benzimidazole compound to fungi or habitats thereof.

DETAILED DESCRIPTION OF THE INVENTION

In the above formula (I),

"a lower alkyl carbamoyl" means a carbamoyl radical with an alkyl group having 1 to 6 carbon atoms of the formula —CONHR$^1$ wherein R$^1$ represents an alkyl group, for example, methyl carbamoyl, ethyl carbamoyl, n-butyl carbamoyl and n-hexyl carbamoyl radicals;

"halogen atoms" include chlorine, bromine and iodine;

"a lower alkyl radical" means an alkyl radical having 1 to 4 carbom atoms such as methyl, ethyl and propyl radicals;

"a lower alkoxy radical" means an alkoxy radical having 1 to 4 carbon atoms such as methoxy and ethoxy radicals;

"a lower alkyl carbamic acid ester" means a lower alkyl carbamic acid ester radical of the formula —NHCOOR$^2$ wherein R$^2$ represents the alkyl group having 1 to 4 carbon atoms.

"acid addition salts" of the compound of formula (I) includes, for example, sulfuric acid, phosphoric acid, nitric acid, hydrochloric acid, p-toluene sulfonic acid and acetic acid salts, and "alkali or alkaline earth metal salts" of the compound of formula (I) includes, for example, sodium, potassium, calcium and magnesium salts of the compound and are represented by the formula:

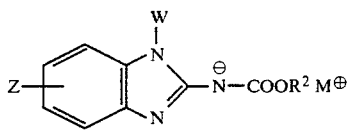

wherein W, Z and R² are as defined above, M⊕ is a cation of alkali meal or alkaline earth metal when Y is a carbamic acid ester.

Among the above benzimidazole compounds, those of formula (I) in which W is a hydrogen or alkyl carbamoyl with an alkyl group having 1 to 6 carbon atoms, Y is carbamic acid ester having 1 to 4 carbon atoms in the alkyl moiety and Z is hydrogen or their acid addition salts are preferred.

Particularly preferred benzimidazole compound is methyl 1-(n-butylcarbamoyl)-2-benzimidazolecarbamate. Methyl 2-benzimidazolecarbamate is also quite preferred.

In the above formula (II), R may be any alkyl radical containing 8 to 20 carbon atoms including decyl, dodecyl, tetradecyl, hexadecyl, octadecyl and eicosyl. These alkyl radicals may be derived from natural sources, for example from coconut oil, beef tallow oil or palm oil or from synthetic alcohols, for example Ziegler alcohols or Oxo alcohols. They may be a mixture containing the pyridinium salts with various carbon atoms. The pyridinium salt may contain, in addition to the alkyl pyridinium salt, alkenyl pyridinium salts such as oleyl pyridinium salt. Preferred pyridinium salts have an alkyl radical with 12 to 16 carbon atoms, especially dodecyl or tetradecyl radicals. X may be any suitable monovalent anion including a halide, for example, chloride or bromide; a sulfonic acid residue, for example, methane sulfonate, benzene sulfonate or toluene sulfonate (tosylate) group; a sulfate acid residue, for example methyl sulfate, ethyl sulfate; and acetate. The most preferred is dodecyl (lauryl) pyridinium halide.

The ratio of the two components in the composition may vary in the wide range so far as the fungicidal activity of the benzimidazole compound is enhanced. Preferably about 0.1 to 10 parts by weight of the alkyl pyridinium salt is incorporated in the composition per part of the benzimidazole compound, and more preferably about ⅓ to 3 parts by weight of the pyridinium salt is used.

The composition of the invention may be in any suitable form for the fungicidal composition with a suitable carrier. It may be in a customary formulation, such as wettable powders, concentrated solutions, granules, emulsions and suspensions. These formulations may be prepared in known manner, for example by mixing the active compounds with carriers, optionally with the use of surface active agents (or emulsifying agents) which are compatible with the alkyl pyridinium salts. As a liquid carrier there may be mentioned water, an organic solvent such as aromatic hydrocarbons, chlorinated hydrocarbons, aliphatic or alicyclic hydrocarbons, alcohols, ketones, ethers and esters. As a solid carrier there may be mentioned ground natural minerals such as kaolins, clays, talc, chalk, quartz and diatomaceous earth and ground synthetic minerals such as highly-dispersed silicic acid, alumina and silicates. As an emulsifying agent there may be mentioned non-ionic emulsifiers such as polyoxyethylene fatty alcohol ethers, polyoxyethylene alkyl phenol ethers and polyoxyethylene fatty acid esters. The formulation normally contains from 0.1 to 90, preferably from 1 to 50%, more preferably from 5 to 30%, by weight of the active ingredient (benzimidazole compound).

According to the invention, the fungicidal benzimidazole compound and the alkyl pyridinium salt may be applied to fungi or habitat thereof in a usual manner. The active compound may be used in the form of the formulations commercially available or in the use form further diluted from the formulations. The active benzimidazole compound content of the use form can vary within wide ranges, the preferred content is from 0.1 ppm to 100,000 ppm and the most preferred content is from 1 to 1,000 ppm. The amount of the active compound to be applied per unit area also varies depending on various conditions, for example, the kind of fungi intended, the stage of the development of the plant, the kind of plant to be protected, the temperature, the humidity and so on. In general the active ingredient benzimidazole is applied 0.01 to 50 kg/ha, and preferably 0.1 to 10 kg/ha.

The following examples illustrate the invention, however these examples should not be regarded as limiting the invention.

Preparation

The alkyl pyridinium salts used in the following examples were synthesized by direct N-alkylation of the pyridine with the desired alkyl compound. The reaction is carried out with the addition of the alkyl chloride to an excess of pyridine and heating the reaction mixture to a temperature between 40° C. and the reflux point, for a length of time between 2 hours and 48 hours, depending on the alkyl reagent used. The product is purified by repeated recrystallizations from acetone or alcohol/ether solutions.

The benzimidazoles were obtained commercially or synthesized.

Benomyl is a commercially available mixture of 50% methyl 1-(n-butylcarbamoyl)-2-benzimidazolecarbamate and 50% sucrose carrier.

EXAMPLE 1

The effects of various concentrations of dodecyl pyridinium chloride in combination with benzimidazoles were studied on the conidia of *Botrytis cinerea* Pers.

The fungicidal activities of dodecyl pyridinium chloride and Benomyl were measured on the conidia of a Benomyl-tolerant strain of *Botrytis cinerea*. The test was designed to assess the fungicidal activity of the alkyl pyridinium alone and of the benzimidazole alone and in their combinations and was replicated three times. Compounds were incorporated into 2% PDA (potato dextrose agar) and poured into 9 cm sterile petri dishes. Conidia were dispersed on the surface of the cooled agar and the amount of germination was measured after 18 hours incubation at 14° C.

Results (Table 1) showed that treatment with 25 ppm Benomyl caused only 2% reduction in germination and that treatment with 25 ppm dodecyl pyridinium chloride led to a 64% reduction. A combination of 25 ppm of both compounds reduced germination by 94%, much more than would be expected through additive effects.

TABLE 1

Germination (%) of conidia of a Benomyl-tolerant strain of *B. cinerea* on 2% PDA after 18 h. incubation at 14° C. Values are mean of 3 replicates (~75 conidia/replicate).

| Benomyl (ppm) | % Germination Dodecyl pyridinium chloride (ppm) | |
|---|---|---|
| | 0 | 25 |
| 0 | 98 | 36 |
| 25 | 97 | 6 |
| 50 | 94 | 4 |
| 75 | 94 | 1 |

EXAMPLE 2

The effects of alkyl pyridinium compounds of various carbon numbers in the alkyl chain in combination with benzimidazoles were studied on the conidia of *Botrytis cinerea* Pers.

The germination values are obtained by a similar procedure to Example 1, using 2% potato dextrose agar medium and after 18 hours of incubation at 16° C. The values are average of three replicates.

The results of this study are summarized in Table II.

| | | Carbon number of alkyl chain in the alkyl pyridinium compounds (APS) | | | | |
|---|---|---|---|---|---|---|
| | | 10 | 12 | 14 | 16 | 18 |
| Critical Micelle Concentration (log ppm) | | 3.89 | 3.05 | 3.03 | 1.23 | 1.94 |
| % germination | 50 ppm Benomyl | 97 | 79 | 91 | 90 | 97 |
| | 50 ppm Benomyl /50 ppm APS | 96 | 1 | 0 | 0 | 61 |

CMC values are approximate median values from the literature—Mukerjee, P. and K. J. Mysels, 1971, Critical Micelle Concentrations of Aqueous Surfactant Systems, U.S. Department of Commerce, NSRDS-NBS 36. Washington, D.C. 222 pp.

It would be apparent from Table II, that alkyl pyridinium compounds used in the present invention are effective to enhance the fungicidal activity of benzimidazole fungicides at a concentration below its CMC value. For example, dodecyl or tetradecyl pyridinium compound may increase the fungicidal activity at the concentration of 50 ppm, which is far below the CMC value of about 1000 ppm.

EXAMPLE 3

The fungicidal activities of dodecyl pyridinium chloride and Benomyl were assessed on the conidia of a Benomyl-tolerant strain of *Monilia fructicola*. The procedure used was the same as that described in Example 1 except that plates were incubated 20 hours at 16° C.

Results (Table III) showed that treatment with 5 ppm Benomyl caused no reduction in germination and that treatment with 5 ppm dodecyl pyridinium chloride caused a 56% reduction. A combination of 5 ppm of both compounds reduced germination by 94%.

TABLE III

Germination (%) of conidia of a Benomyl-tolerant strain of *M. fructicola* of 2% PDA after 20 hr. incubation at 16° C. Values are mean of 3 replicates (~75 conidia/replicate).

| Benomyl (ppm) | % Germination Dodecyl Pyridinium Chloride (ppm) | |
|---|---|---|
| | 0 | 5 |
| 0 | 95 | 44 |
| 5 | 95 | 6 |
| 10 | 91 | 3 |
| 25 | 88 | 3 |

EXAMPLE 4

The synergistic activity of dodecyl pyridinium chloride (C) was compared with quarternary ammonium cationic compounds having one or two long chain alkyl groups. As the cationic surfactants, benzyldimethylhexadecyl ammonium chloride (A) and dimethyldistearyl ammonium chloride (B) were selected.

The test compound with or without Benomyl was incorporated into autoclaved 2% PDA and poured into 9 cm petri dishes. The medium was then incubated with conidia of a Benomyl-tolerant strain of *Botrytis cinerea*. The test was designed in a 4×4 matrix with 3 replicates per compounds of each of the treatments.

Germination of conidia was assessed after 18 hour incubation at 14° C. The results are shown in Table IV and V below.

TABLE IV

Germination (%) of conidia of a Benomyl-tolerant strain of *B. cinerea* on 2% PDA.

| Benomyl (ppm) | APS12C (ppm) | | |
|---|---|---|---|
| | 0 | 25 | 50 |
| 0 | 92 | 92 | 60 |
| 25 | 94 | 30 | 1 |
| 50 | 92 | 10 | 0 |

TABLE V

Germination of conidia of a Benomyl-tolerant strain of *B. cinerea* on 2% PDA amended with: A - benzyldimethyl hexadecyl ammonium chloride, B - dimethyl distearyl ammonium chloride.

| Treatment (ppm) | Germination (%) | |
|---|---|---|
| | A | B |
| Control | 95 | 92 |
| 50 A, B | 90 | 98 |
| 100 A, B | 88 | 99 |
| 250 A, B | 89 | 99 |
| 50 Benomyl | 94 | 87 |
| 50 A, B/50 Benomyl | 89 | 98 |
| 100 A, B/50 Benomyl | 93 | 99 |
| 250 A, B/50 Benomyl | 81 | 99 |
| 100 Benomyl | 97 | 99 |
| 50 A, B/100 Benomyl | 97 | 100 |
| 100 A, B/100 Benomyl | 96 | 100 |
| 250 A, B/100 Benomyl | 97 | 97 |
| 250 Benomyl | 94 | 100 |
| 50 A, B/250 Benomyl | 89 | 100 |
| 100 A, B/250 Benomyl | 93 | 100 |
| 250 A, B/250 Benomyl | 97 | * |

*Medium was too dense to see through with microscope

It will be apparent from Tables IV and V, that alkyl pyridinium compound has a strong synergistic activity when combined with benzimidazole fungicide, even at a quite low concentration (as low as 25 ppm), whereas this effect can not be attained with either Benomyl/benzyldimethylhexadecyl ammonium chloride or dimethyl distearyl ammonium chloride even though these compounds were used at much higher concentrations than dodecyl pyridinium chloride. Neither compound A or B has any effect on conidial germination at concentrations up to 250 ppm with 250 ppm Benomyl.

What is claimed is:

1. A fungicidal composition with increased fungicidal activity, against benomyl tolerant fungi comprising (A) 0.1 to 90% by weight of methyl 1-(n-butylcarbamoyl)-2-benzimidazolecarbamate, and (B) 0.2 to 2 parts by weight of an alkyl pyridinium salt with the formula:

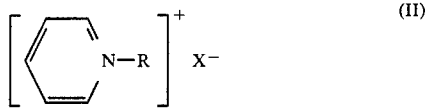
(II)

wherein R represents an alkyl radical containing 12 to 16 carbon atoms and X is a monovalent anion, per part of the benzimidazole, wherein the composition is formulated such that when a further diluted aqueous solution containing 1 to 1,000 ppm of the benzimidazole insecticide is applied to fungi or habitats thereof, the concentration of the alkyl pyridinium salt in the diluted aqueous solution is below its critical micelle concentration level.

2. A composition according to claim 1, wherein the alkyl pyridinium salt is dodecyl pyridinium chloride or bromide, tetradecyl pyridinium chloride or bromide, or a mixture thereof.

3. A composition according to claim 2, wherein the amount of the alkyl pyridinium chloride is ⅓ to 3 parts by weight per part of the benzimidazole compound.

4. A method of combatting strains of Benomyl tolerant or resistant fungi, which comprises applying to fungi or habitats thereof an aqueous solution containing 1 to 1,000 ppm of methyl 1-(n-butylcarbamoyl)-2-benzimidazolecarbamate and an alkyl pyridinium salt of the formula:

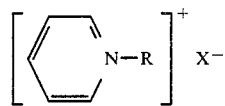

wherein R represents an alkyl radical containing 12 to 16 carbon atoms and $X^-$ is a monovalent anion, wherein the amount of the alkyl pyridinium salt is 0.2 to 2.0 parts by weight per part of the benzimidazole fungicide provided that the concentration of the alkyl pyridinium salt in the aqueous solution is below the critical micelle concentration level.

5. A method according to claim 4, wherein the aqueous solution is applied to a plant.

6. A method according to claim 5, wherein the aqueous solution is applied to benzimidazole-tolerant or -resistant fungi.

7. A method according to claim 5, wherein the alkyl pyridinium salt is dodecyl pyridinium chloride or bromide, tetradecyl pyridinium chloride or bromide or a mixture thereof.

8. A method according to claim 7, wherein the aqueous solution is applied such that the benzimidazole fungicide is applied 0.1 to 10 kg/ha.

9. A method according to claim 7, wherein the aqueous solution is applied to Benomyl tolerant or resistant strains of *Botrytis cinerea* or *Monilia fructicola*.

* * * * *